United States Patent
Meng et al.

(10) Patent No.: US 12,390,277 B2
(45) Date of Patent: Aug. 19, 2025

(54) PULP DIAGNOSIS-TREATMENT ASSISTANCE METHOD AND SYSTEM BASED ON DIGITAL DYNAMIC GUIDE

(71) Applicant: WUHAN UNIVERSITY, Hubei (CN)

(72) Inventors: Liuyan Meng, Hubei (CN); Weiwei Qiao, Hubei (CN); Xiaonan Wang, Hubei (CN); Zhuan Bian, Hubei (CN)

(73) Assignee: WUHAM UNIVERSITY, Hubei (CN)

( * ) Notice: Subject to any disclaimer, the term of this patent is extended or adjusted under 35 U.S.C. 154(b) by 307 days.

(21) Appl. No.: 18/352,275

(22) Filed: Jul. 14, 2023

(65) Prior Publication Data
US 2024/0033006 A1    Feb. 1, 2024

(30) Foreign Application Priority Data
Jul. 27, 2022 (CN) .......................... 202210893135.X (51) Int. Cl.
*A61B 34/10* (2016.01)
*A61B 5/00* (2006.01)
(Continued)

(52) U.S. Cl.
CPC ............ *A61B 34/10* (2016.02); *A61B 5/4547* (2013.01); *A61B 34/20* (2016.02); *A61B 90/36* (2016.02);
(Continued)

(58) Field of Classification Search
CPC ....... A61B 34/10; A61B 5/4547; A61B 34/20; A61B 90/36; A61B 2034/2065; A61B 2090/365; A61B 6/032; A61B 6/4085; A61B 6/4417; A61B 6/5247; A61B 90/20; A61B 2090/372; A61B 2090/373; A61B 2090/3764; A61B 5/0088; A61B 6/51;
(Continued)

(56) References Cited

U.S. PATENT DOCUMENTS

10,213,274 B1 * 2/2019 Alshawi ................. A61B 34/20
2012/0214121 A1 * 8/2012 Greenberg ........... A61B 6/5247
433/213
(Continued)

*Primary Examiner* — Solomon G Bezuayehu
(74) *Attorney, Agent, or Firm* — JCIP GLOBAL INC.

(57) ABSTRACT

A pulp diagnosis-treatment assistance method and system are disclosure, and relates to the field of medical device technologies. The method includes: based on CBCT three-dimensional reconstruction data and three-dimensional model data of an oral scanner corresponding to an oral cavity of a patient, obtaining integrated and registered three-dimensional model data; obtaining a digital scanning image of an oral microscope corresponding to the oral cavity; based on the CBCT three-dimensional reconstruction data corresponding to the oral cavity of the patient and a pre-surgical designed surgical path, obtaining position information of surgical appliance and relative position information of surgical zone; based on the integrated and registered three-dimensional model data, the digital scanning image of the oral microscope, the position information of the surgical appliance, and the relative position information of the surgical zone, obtaining a diagnosis-treatment assistance image, and based on the diagnosis-treatment assistance image. performing pulp diagnosis and treatment assistance.

10 Claims, 8 Drawing Sheets

(51) Int. Cl.
   *A61B 34/20* (2016.01)
   *A61B 90/00* (2016.01)
   *G06T 7/00* (2017.01)
(52) U.S. Cl.
   CPC ...... *G06T 7/0012* (2013.01); *A61B 2034/105* (2016.02); *A61B 2034/2065* (2016.02); *A61B 2090/365* (2016.02); *G06T 2207/30036* (2013.01)
(58) Field of Classification Search
   CPC .. A61B 2034/2055; G06T 2207/30036; G06T 2207/10056; G06T 2207/10081
   See application file for complete search history.

(56) References Cited

U.S. PATENT DOCUMENTS

| | | | |
|---|---|---|---|
| 2013/0171580 A1* | 7/2013 | Van Lierde | A61B 6/481 433/29 |
| 2020/0100881 A1* | 4/2020 | Emery, III | A61C 8/0009 |
| 2021/0192759 A1* | 6/2021 | Lang | A61B 34/10 |
| 2021/0244372 A1* | 8/2021 | Inglese | A61B 6/463 |
| 2021/0244374 A1* | 8/2021 | Zhao | A61B 6/4241 |
| 2022/0165388 A1* | 5/2022 | Chernov | G16H 30/20 |
| 2022/0202295 A1* | 6/2022 | Elbaz | G16H 30/40 |
| 2022/0323190 A1* | 10/2022 | Kopelman | A61C 9/0053 |
| 2023/0126119 A1* | 4/2023 | Koski | A61C 9/0006 433/214 |
| 2024/0108416 A1* | 4/2024 | Wang | A61B 5/0088 |
| 2024/0320935 A1* | 9/2024 | Pissarenko | A61B 34/25 |

* cited by examiner

PULP DIAGNOSIS-TREATMENT ASSISTANCE METHOD AND SYSTEM BASED ON DIGITAL DYNAMIC GUIDE

CROSS-REFERENCE TO RELATED APPLICATION

This application claims the priority benefit of China application serial no. 202210893135.X filed on Jul. 27, 2022. The entirety of the above-mentioned patent application is hereby incorporated by reference herein and made a part of this specification.

BACKGROUND

Technical Field

The present disclosure relates to the field of medical device technologies, and in particular to a pulp diagnosis-treatment assistance method and system based on digital dynamic guide.

Description of Related Art

Pulp disease and periapical disease are common and frequently-occurring in oral clinic. Root canal treatment is an effective method for treating such diseases. The root canal treatment includes the flowing steps: endodontic access, root canal preparation, root canal washing, and root canal filling, and so forth, each of steps can affect the quality of the root canal treatment. The endodontic access and the root canal preparation are the first step for root canal treatment as well as a critical technology for successful treatment. Due to such as the frequently-occurring number and structures of the root canals, and so forth anatomical variations, pulp calcification, and so forth makes it difficult to position the root canal orifice and difficult to dredge the root canals, thus increasing the difficulty of root canal preparation and thus affecting the success rate of the root canal treatment. When the root canal treatment or re-treatment fails, the treated tooth has serious anatomical variation of root canal, or it is desired to clearly determine the diagnosis through exploratory surgery or so forth, it is usually required to perform endodontic surgery, namely, remove periapical lesion tissues, cut off apical infection, cut off partial infected apical tissues, and clean and close the apical zone to promote the treatment of the periapical disease.

At present, in the clinic, the determination of the anatomical structure of the root canal systems and the periapical tissues is mainly dependent on apical films, panoramic tomography films and CBCT (Cone Beam Computerized Tomography) auxiliary examination, and based on their experiences, doctors perform abstract stereoscopic construction and cognition on two-dimensional or three-dimensional pictures provided by imageological examination and then combine it with the true oral environment of the patients.

Although the applications of the CBCT and the dental operating microscope increase the success rate of the treatments for the dental pulp diseases. However, due to different personal clinical experiences and limitation of three-dimensional structural cognition capability, the cognition of the doctors for the anatomical structure of the root canal systems and the periapical tissues still uncertain. In a case of difficult diseases, insufficient experiences of the doctors, dental structural variations, or so forth, an effective method is desired to perform effective real-time guide for a treated tooth for direct operation guidance, and perform clear and full positioning on the root canal and the apex of the treated tooth in real time.

Therefore, in order to satisfy the actual use requirements, a pulp diagnosis-treatment assistance technology based on digital dynamic guide is provided.

SUMMARY

The present disclosure provides a pulp diagnosis-treatment assistance method and system based on digital dynamic guide. In the method and system, based on CBCT, an oral scanner and an oral microscope, three-dimensional construction of an oral model is performed and color partitioning is performed on different zones of the three-dimensional perspective model or registration and calibration are performed on the oral cavity of the patients and the appliance of the surgeons by using a navigator to position a surgical appliance in real time, such that the medical staff can accurately know where the surgical appliance is. In this way, the medical staff is assisted in performing pulp diagnosis and treatment.

According to a first aspect, the present disclosure provide a pulp diagnosis-treatment assistance method based on digital dynamic guide. The method includes the following steps:

based on CBCT three-dimensional reconstruction data and three-dimensional model data of an oral scanner corresponding to an oral cavity of a patient, obtaining integrated and registered three-dimensional model data;

obtaining a digital scanning image of an oral microscope corresponding to the oral cavity of the patient;

based on the CBCT three-dimensional reconstruction data corresponding to the oral cavity of the patient and a pre-surgical designed surgical path, obtaining position information of a surgical appliance and relative position information of a surgical zone;

based on the integrated and registered three-dimensional model data, the digital scanning image of the oral microscope, the position information of the surgical appliance and the relative position information of the surgical zone, obtaining a diagnosis-treatment assistance image, and based on the diagnosis-treatment assistance image, performing pulp diagnosis and treatment assistance.

In an embodiment, based on the integrated and registered three-dimensional model data, the digital scanning image of the oral microscope, the position information of the surgical appliance and the relative position information of the surgical zone, obtaining a diagnosis-treatment assistance image, and based on the diagnosis-treatment assistance image, performing pulp diagnosis and treatment assistance comprise the following steps:

based on the integrated and registered three-dimensional model data, the digital scanning image of the oral microscope, the position information of the surgical appliance and the relative position information of the surgical zone, obtaining a corresponding diagnosis-treatment assistance image;

displaying the diagnosis-treatment assistance image by a display device.

In an embodiment, the display device is a naked eye 3D display.

In an embodiment, based on the integrated and registered three-dimensional model data, the digital scanning image of the oral microscope, the position information of the surgical appliance and the relative position information of the surgical zone, obtaining a diagnosis-treatment assistance image, and based on the diagnosis-treatment assistance image, performing pulp diagnosis and treatment assistance comprise the following steps:

based on the integrated and registered three-dimensional model data, the position information of the surgical appliance, and the relative position information of the surgical zone, performing image superimposition to obtain a corresponding integrated and registered three-dimensional optical image; and, based on the integrated and registered three-dimensional optical image and the digital scanning image of the oral microscope, obtaining a corresponding diagnosis-treatment assistance image;

observing the diagnosis-treatment assistance image by using a microscopic ocular.

In an embodiment, the microscopic ocular is configured to be in the form of head-mounted AR display device.

In an embodiment, the CBCT three-dimensional reconstruction data is obtained by performing detection on the oral cavity of the patient using a CBCT device before pulp diagnosis and treatment;

the three-dimensional model data of the oral scanner is obtained by performing detection on the oral cavity of the patient using the oral scanner before pulp diagnosis and treatment.

According to a second aspect, the present disclosure provide a pulp diagnosis-treatment assistance system based on digital dynamic guide, comprising:

a CBCT device, configured to detect and obtain CBCT three-dimensional reconstruction data corresponding to an oral cavity of a patient;

an oral scanner, configured to detect and obtain three-dimensional model data of the oral scanner corresponding to the oral cavity of the patient;

an oral microscope, configured to detect and obtain a digital scanning image of the oral microscope corresponding to the oral cavity of the patient;

an image integrating apparatus, configured to, based on the CBCT three-dimensional reconstruction data corresponding to the oral cavity of the patient and the three-dimensional model data of the oral scanner corresponding to the oral cavity of the patient, obtain integrated and registered three-dimensional model data;

a navigator, configured to detect and obtain position information of a surgical appliance and relative position information of a surgical zone;

wherein the image integrating apparatus is further configured to, based on the integrated and registered three-dimensional model data, the digital scanning image of the oral microscope, the position information of the surgical appliance and the relative position information of the surgical zone, obtain a diagnosis-treatment assistance image;

an image displaying apparatus, configured to display the diagnosis-treatment assistance image.

In an embodiment, the image displaying apparatus is a naked eye 3D display.

In an embodiment, the image displaying apparatus is a microscopic ocular; the microscopic ocular is configured to be in the form of head-mounted AR display device.

In an embodiment, the CBCT three-dimensional reconstruction data is obtained by performing detection on the oral cavity of the patient using a CBCT device before pulp diagnosis and treatment;

the three-dimensional model data of the oral scanner is obtained by performing detection on the oral cavity of the patient using the oral scanner before pulp diagnosis and treatment.

The technical solution provided by the present disclosure has the following beneficial effects:

based on CBCT, an oral scanner, and an oral microscope, performing three-dimensional construction of an oral model, performing color partitioning on different zones of the three-dimensional perspective model, or performing registration and calibration on the oral cavity of the patients and the appliance of the surgeons by using a navigator to position surgical appliance in real time, such that the medical staff can accurately know where the surgical appliance is. In this way, the medical staff is assisted in performing pulp diagnosis and treatment.

BRIEF DESCRIPTION OF THE DRAWINGS

Term Interpretations

CBCT: Cone beam Computer Tomography
AR: Augmented Reality.

In order to more clearly describe the technical solutions in the embodiments of the present disclosure, drawings required for descriptions of the embodiments will be briefly introduced below. Apparently, the drawings described hereunder are only some embodiments of the present disclosure. One of ordinary skill in the art can also obtain other drawings based on these drawings without any creative efforts.

DESCRIPTIONS OF THE EMBODIMENTS

In order to make the objects, the technical solutions, and the advantages of the embodiments of the present disclosure clearer, the technical solution of the embodiments of the present disclosure will be fully and clearly described below in combination with the drawings in the embodiments of the present disclosure. Apparently, the embodiments described herein are merely some embodiments rather than all embodiments. All other embodiments obtained by one of ordinary skill in the art without making any creative efforts shall belong to the scope of protection the present disclosure.

The embodiments of the present disclosure accompanied with drawings are described in detail below.

An embodiment of the present disclosure provides a pulp diagnosis-treatment assistance method and system based on digital dynamic guide. In the method and system, based on CBCT, an oral scanner and an oral microscope, three-dimensional construction of an oral model is performed, color partitioning is performed on different zones of the three-dimensional perspective model, and/or registration and calibration are performed on the oral cavity of the patients and the appliance of the surgeons by using a navigator to position surgical appliance in real time, such that the medical staff can accurately know where the surgical appliance is. In this way, the medical staff is assisted in performing pulp diagnosis and treatment.

In order to achieve the above technical effect, the overall thought of the present disclosure is as shown below.

There is provided a pulp diagnosis-treatment assistance method based on digital dynamic guide, which includes the following steps.

In step S1, based on CBCT three-dimensional reconstruction data and three-dimensional model data of an oral scanner corresponding to an oral cavity of a patient, integrated and registered three-dimensional model data is obtained.

In step S2, a digital scanning image of an oral microscope corresponding to the oral cavity of the patient is obtained.

In step S3, based on the CBCT three-dimensional reconstruction data corresponding to the oral cavity of the patient and a pre-surgical designed surgical path, position information of a surgical appliance and relative position information of a surgical zone are obtained.

In step S4, based on the integrated and registered three-dimensional model data, the digital scanning image of the oral microscope, the position information of the surgical appliance and the relative position information of the surgical zone, a diagnosis-treatment assistance image is obtained, and based on the diagnosis-treatment assistance image, pulp diagnosis and treatment assistance are performed.

The embodiment of the present disclosure will be further elaborated below in combination with drawings.

According to a first aspect of embodiments, as shown in FIGS. 1 to 4, there is provided a pulp diagnosis-treatment assistance method based on digital dynamic guide. The method includes the following steps.

Figure 1:
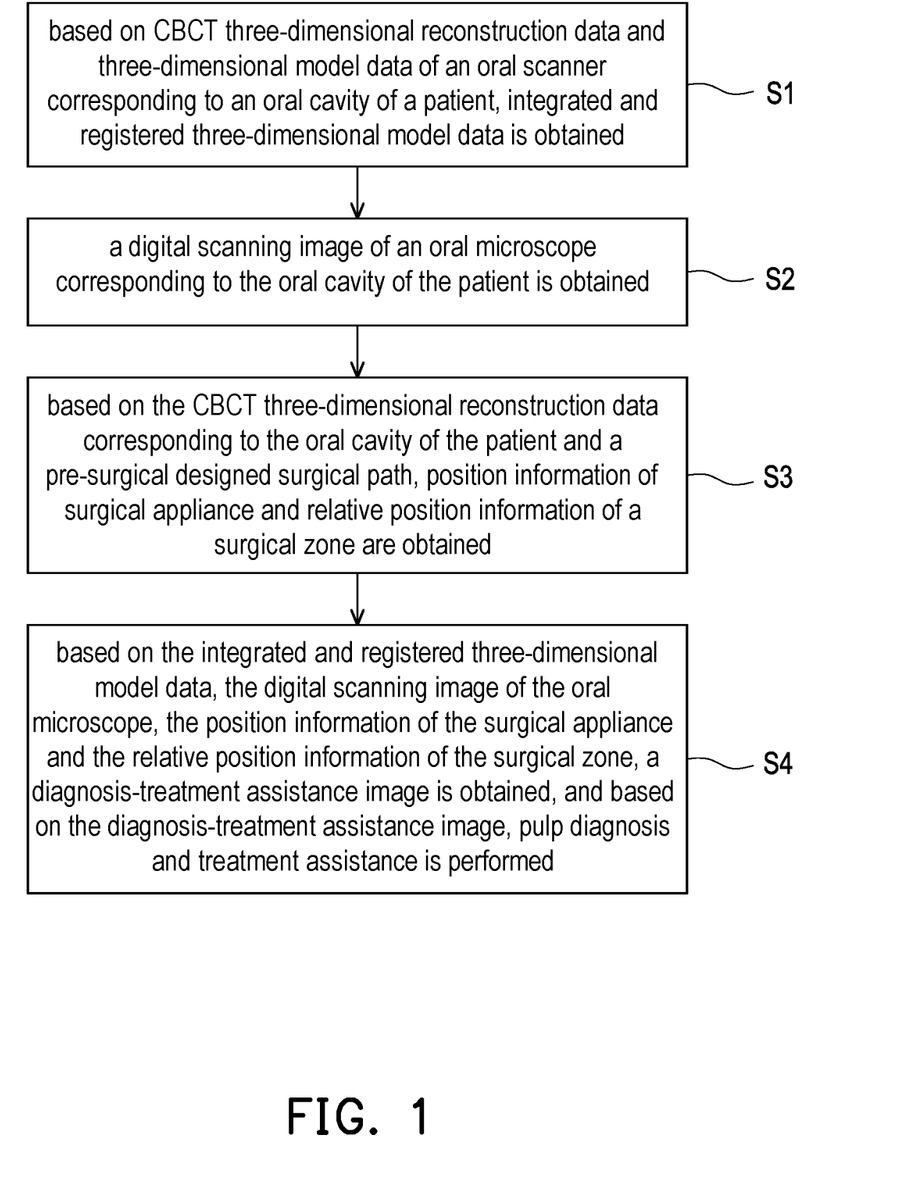
FIG. 1 is a flowchart illustrating steps of a pulp diagnosis-treatment assistance method based on digital dynamic guide according to an embodiment of the present disclosure.
Figure 2:
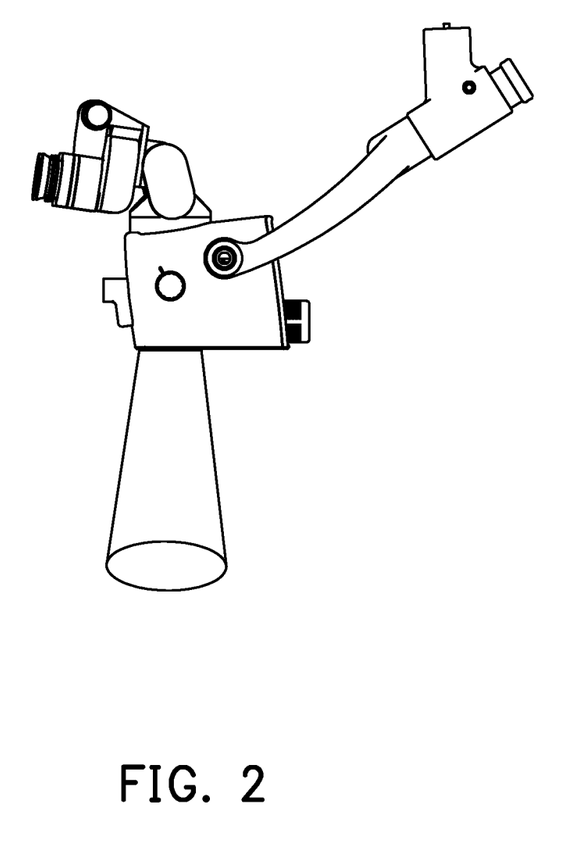
FIG. 2 is a schematic diagram illustrating operation of an oral microscope in a pulp diagnosis-treatment assistance method based on digital dynamic guide according to an embodiment of the present disclosure.
Figure 3:
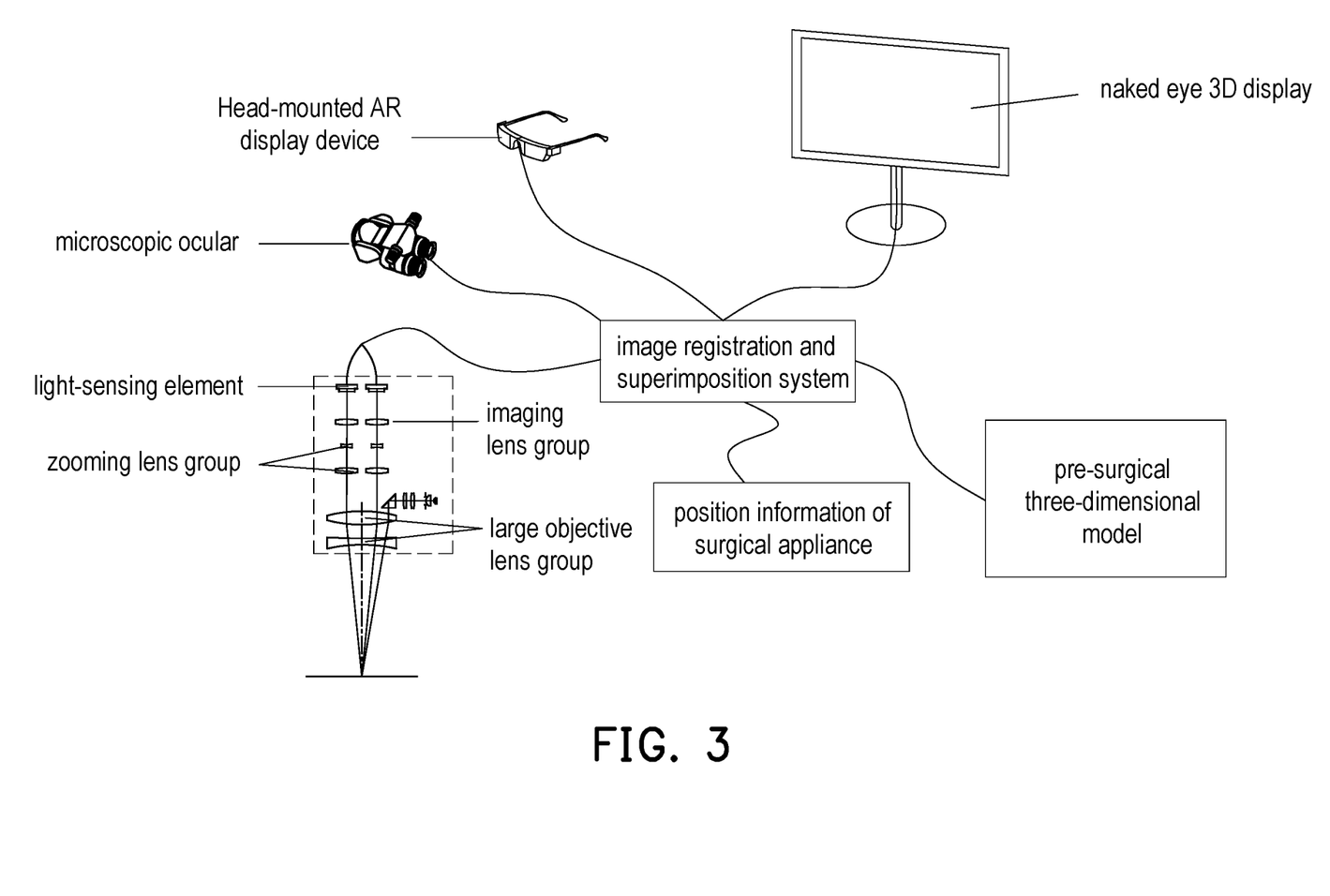
FIG. 3 is a schematic diagram illustrating operation of a pulp diagnosis-treatment assistance method based on digital dynamic guide according to an embodiment of the present disclosure.

In step S1, based on CBCT three-dimensional reconstruction data and three-dimensional model data of an oral scanner corresponding to an oral cavity of a patient, integrated and registered three-dimensional model data is obtained.

In step S2, a digital scanning image of an oral microscope corresponding to the oral cavity of the patient is obtained.

In step S3, based on the CBCT three-dimensional reconstruction data corresponding to the oral cavity of the patient and a pre-surgical designed surgical path, position information of surgical appliance and relative position information of a surgical zone are obtained.

In step S4, based on the integrated and registered three-dimensional model data, the digital scanning image of the oral microscope, the position information of the surgical appliance and the relative position information of the surgical zone, a diagnosis-treatment assistance image is obtained, and based on the diagnosis-treatment assistance image, pulp diagnosis and treatment assistance are performed.

It is noted that, based on the CBCT three-dimensional reconstruction data and the three-dimensional model data of the oral scanner corresponding to the oral cavity of the patient, the position information of the oral cavity of the patient and the surgical appliance can be obtained by using the calibration and registration technology and navigator technology.

The technical solution of the embodiments of the present disclosure includes the following two cases.

In a first case, three-dimensional reconstruction image registration is performed on a dental image under CBCT, the oral scanner and the oral the microscope to form a three-dimensional perspective image and different colors are used to distinguish different tissue zones.

Image information can be displayed by a 3D naked eye display screen, a microscopic ocular, and VR glasses.

In this case, it is not required to position the surgical appliance.

In a second case, pre-surgical path planning is performed based on the CBCT three-dimensional reconstruction data corresponding to the oral cavity of the patient, and based on calibration and registration and navigator technology, the position information of the surgical zone of the oral cavity of the patient and the surgical appliance is obtained.

The position information can be displayed by a 3D naked eye display screen, a microscopic ocular, and VR glasses.

In the embodiments of the present disclosure, based on CBCT, the oral scanner and the oral microscope, three-dimensional reconstruction of the oral model is performed such that the medical staff can accurately know where the surgical appliance is based on the positioning technology of the surgical appliance. In this way, the medical staff is assisted in performing pulp diagnosis and treatment.

Specifically, based on the integrated and registered three-dimensional model data, the digital scanning image of the oral microscope, the position information of the surgical appliance, and the relative position information of the surgical zone, a diagnosis-treatment assistance image is obtained, and based on the diagnosis-treatment assistance image, pulp diagnosis and treatment assistance are performed, which includes the following steps:

based on the integrated and registered three-dimensional model data, the digital scanning image of the oral microscope, the position information of the surgical appliance, and the relative position information of the surgical zone, obtaining a corresponding diagnosis-treatment assistance image is obtained; and     displaying the diagnosis-treatment assistance image by a display device.

Preferably, the display device is a naked eye 3D display.

Specifically, based on the integrated and registered three-dimensional model data, the digital scanning image of the oral microscope, the position information of the surgical appliance and the relative position information of the surgical zone, a diagnosis-treatment assistance image is obtained, and based on the diagnosis-treatment assistance image, pulp diagnosis and treatment assistance are performed, which includes the following steps:

based on the integrated and registered three-dimensional model data, the position information of the surgical appliance, and the relative position information of the surgical zone, performing image superimposition to obtain a corresponding integrated and registered three-dimensional optical image;

based on the integrated and registered three-dimensional optical image and the digital scanning image of the oral microscope, obtaining a corresponding diagnosis-treatment assistance image;

observing the diagnosis-treatment assistance image by using a microscopic ocular.

Preferably, the microscopic ocular is configured to be in the form of head-mounted AR display device.

Specifically, the CBCT three-dimensional reconstruction data is obtained by performing detection on the oral cavity of the patient using the CBCT device before pulp diagnosis and treatment.

The three-dimensional model data of the oral scanner is obtained by performing detection on the oral cavity of the patient using the oral scanner before pulp diagnosis and treatment.

Based on the technical solution provide by the embodiments of the present disclosure, one of implementation is described below.

First of all, a CBCT image of the oral cavity of the patient, i.e. the CBCT three-dimensional reconstruction data and the data of the oral scanner, i.e. the three-dimensional model data of the oral scanner are received, and analyzed by using a preset signal processing apparatus. Then comparison of biological characteristics is performed based on image processing algorithm to perform integration and registration based on feature points, so as to obtain an accurate three-dimensional perspective model image of the oral cavity of the target object. Thus the integrated and registered three-dimensional model data is obtained.

The oral CBCT image has the stereoscopic perspective and low-resolution characteristics, whereas the data of the oral scanner has the stereoscopic non-perspective and high-resolution characteristics.

Secondly, a three-dimensional digital image is obtained by collecting an optical image under the oral microscope, namely, the digital scanning image of the oral microscope is obtained and then observed by the head-mounted AR display device or the naked eye 3D display, or directly displayed in the field of view of the operator in the form of optical image by the microscopic ocular.

When wearing the AR display device or the naked eye 3D display, the doctor can move his head freely no longer limited by the position of the surgical microscope, and can simultaneously observe the under-microscope magnified field of view and outside-microscope normal field of view, the surgical appliance being continuously visible and accurately being moved to a specified position under the microscope.

Figure 4:
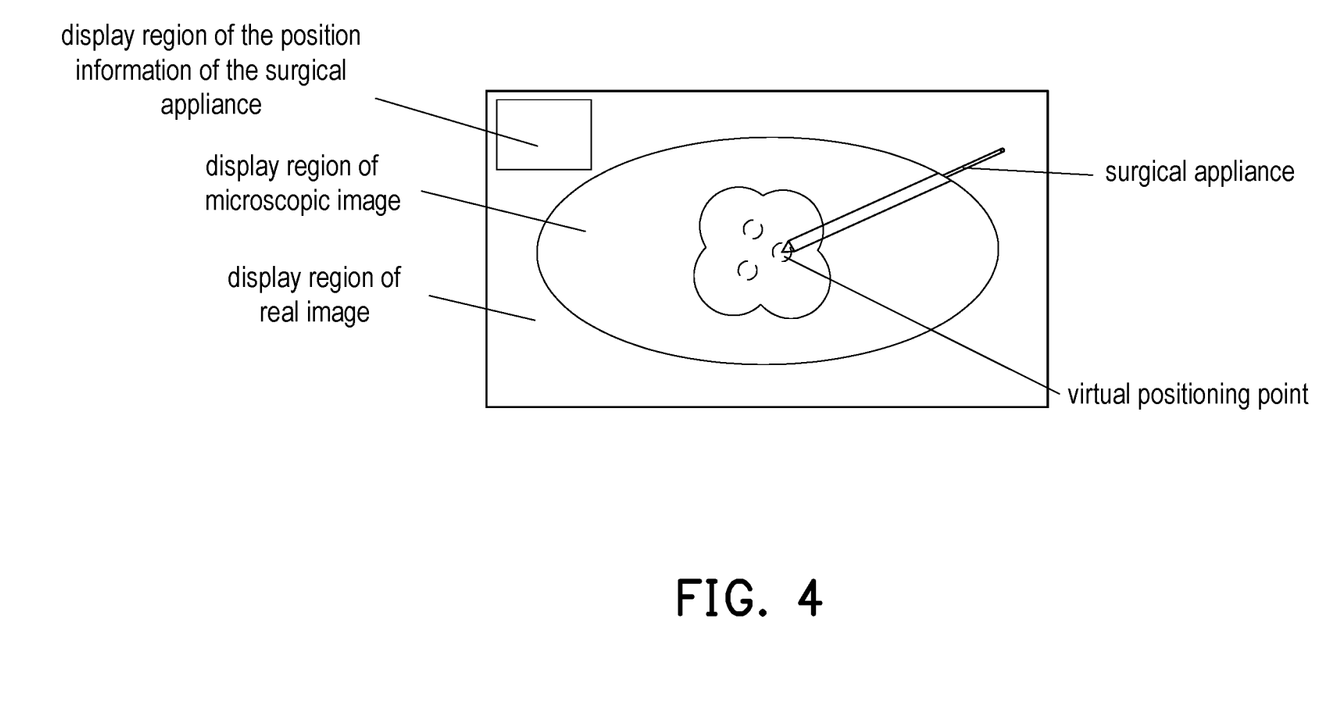
FIG. 4 is a schematic diagram illustrating an observation effect of a display device in a pulp diagnosis-treatment assistance method based on digital dynamic guide according to an embodiment of the present disclosure.

As shown in FIG. 4, the under-microscope magnified field of view is the display region of a display module in the AR, the naked eye 3D display and the ocular, and the outside-microscope normal field of view is a display region of a real image displayed by a non-display module.

At the same time, a patient state can be observed or guidance is provided to a nurse to confirm the appliance or material is correct.

An image split screen display module displays the above information on the head-mounted AR display device or the naked eye 3D display or the ocular display device in superimposition form. Each display window can be opened or closed, and their sizes and positions can be adjustable, and if necessary, four views can be generated, which are three plane views of sections of three directions and one stereoscopic perspective view to display relative position information of the surgical appliance and the target object. The doctor can mark a virtual positioning point on the model, for example, the position of the root canal orifice, the endodontic access, the window opening position, the removal scope, and so forth, so as to guide various operations.

The guiding way may be performed in the following two methods.

In a first method, color partitioning is performed on different tissues of the surgical zone, such that the operator can observe, in real time, the operation position of the appliance under the microscope through the head-mounted AR and the naked eye 3D display.

In a second method, marking designing is performed in advance for the operation path before surgery, and then three-dimensional perspective model registration is performed. The pre-surgical planned path can be displayed through display devices such as head-mounted AR, naked eye 3D display, and so forth to guide the operator in surgical operation.

Marking designing is performed in advance for the operation path before surgery, and registration and calibration are performed for the oral tissues and the surgical appliance; corresponding positions of the surgical zones of the surgical appliance are tracked by using the navigator; the pre-surgical planned path can be displayed through display devices such as head-mounted AR, naked eye 3D display, and so forth to guide the operator in surgical operation.

In the embodiments of the present disclosure, the optical image under the dental microscope is displayed in the field of view of the operator in the form of optical image, and the operation space of the doctor will no longer be affected by the position of the microscope. In the meantime, the state of the patient can be observed and guidance is provided for other surgical personnel.

The integrated and registered three-dimensional model data can be superimposed with the digital scanning image of the oral microscope for displaying, and a positioning and navigation detection apparatus is disposed in the surgical appliance to obtain the digital scanning image of the oral microscope to guide accurate surgical operation. In this way, minimally-invasive, accurately-controllable, and visually-efficient dental pulp operation based on three-dimensional digital guide can be achieved under the oral microscope.

Figure 5:
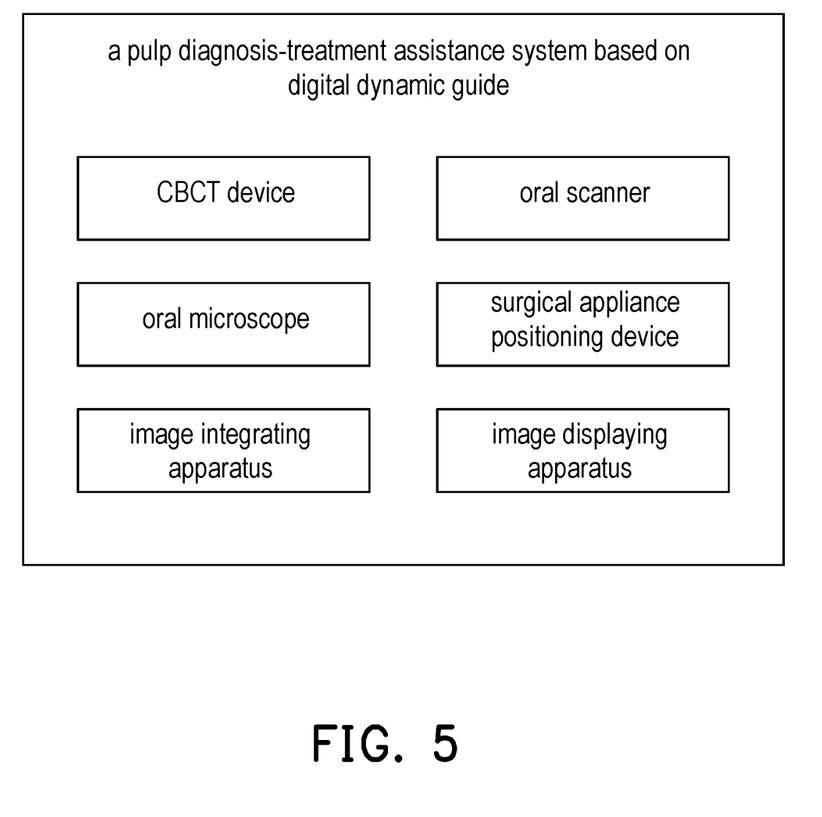
FIG. 5 is a structural block diagram illustrating a pulp diagnosis-treatment assistance system based on digital dynamic guide according to an embodiment of the present disclosure.

Secondly, as shown in FIGS. 5 to 8, on the basis of the technology of the pulp diagnosis-treatment assistance method based on digital dynamic guide as described in the first aspect of embodiments of the present disclosure, there is provided a pulp diagnosis-treatment assistance system based on digital dynamic guide, which includes:

a CBCT device, configured to detect and obtain CBCT three-dimensional reconstruction data corresponding to an oral cavity of a patient;

an oral scanner, configured to detect and obtain three-dimensional model data of the oral scanner corresponding to the oral cavity of the patient;

an oral microscope, configured to detect and obtain a digital scanning image of the oral microscope corresponding to the oral cavity of the patient;

an image integrating apparatus, configured to, based on the CBCT three-dimensional reconstruction data corresponding to the oral cavity of the patient and the three-dimensional model data of the oral scanner corresponding to the oral cavity of the patient, obtain integrated and registered three-dimensional model data;

a navigator, configured to detect and obtain position information of surgical appliance and relative position information of a surgical zone;

wherein the image integrating apparatus is further configured to, based on the integrated and registered three-dimensional model data, the digital scanning image of the oral microscope, the position information of the surgical appliance and the relative position information of the surgical zone, a diagnosis-treatment assistance image is obtained;

an image displaying apparatus, configured to display the diagnosis-treatment assistance image.

Figure 6:
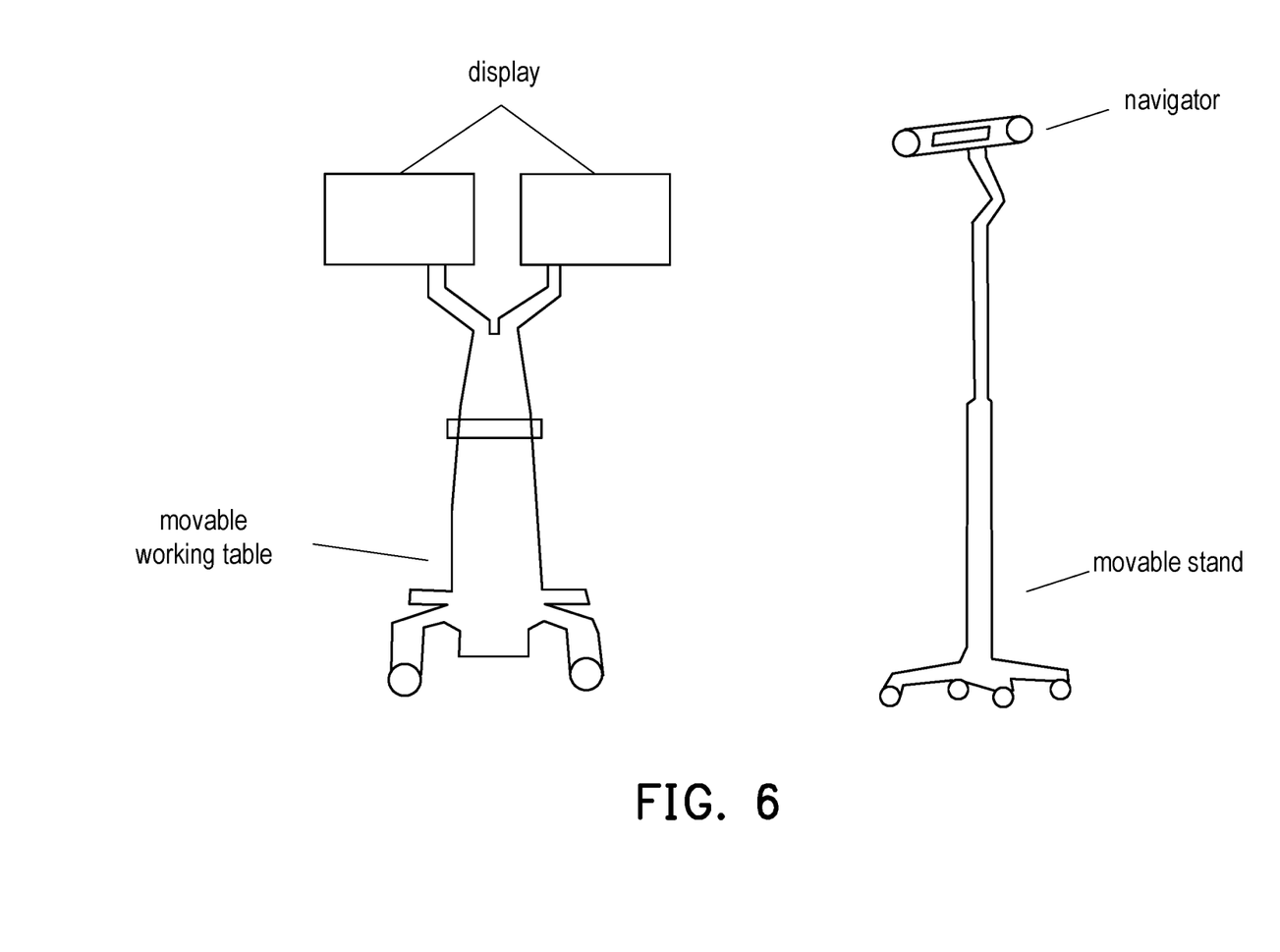
FIG. 6 is a schematic diagram illustrating a navigator and a display in a pulp diagnosis-treatment assistance system based on digital dynamic guide according to an embodiment of the present disclosure.
Figure 7:
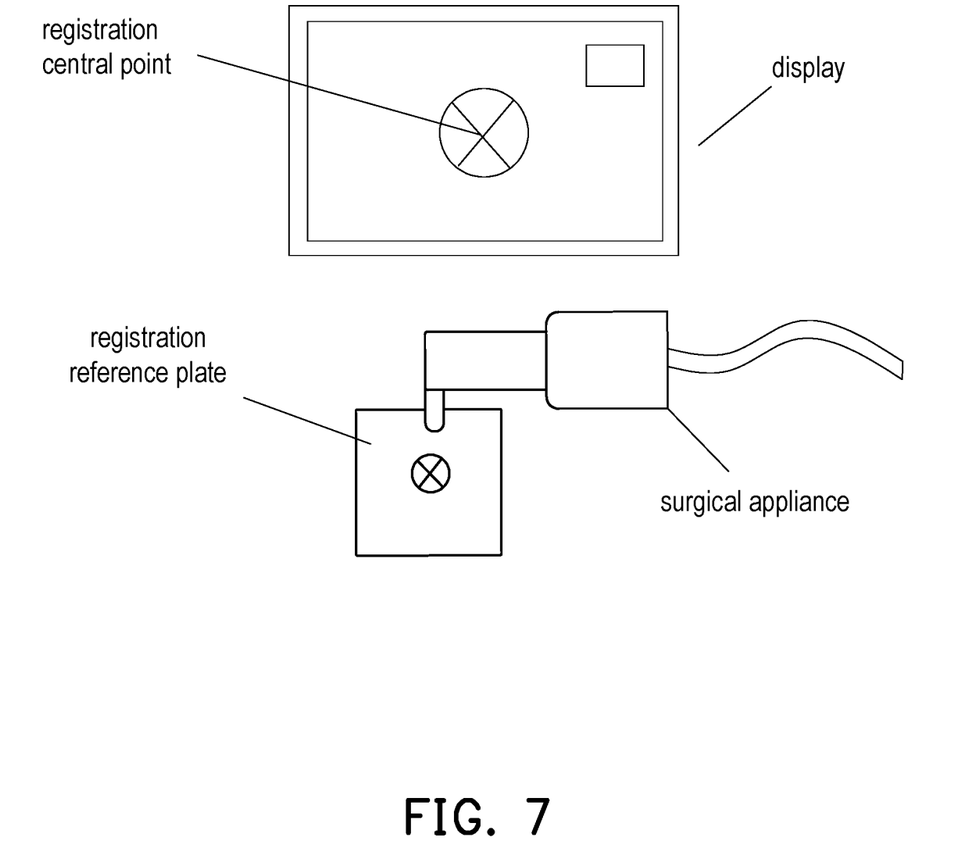
FIG. 7 is a schematic diagram illustrating a registration reference plate in a pulp diagnosis-treatment assistance system based on digital dynamic guide according to an embodiment of the present disclosure.
Figure 8:
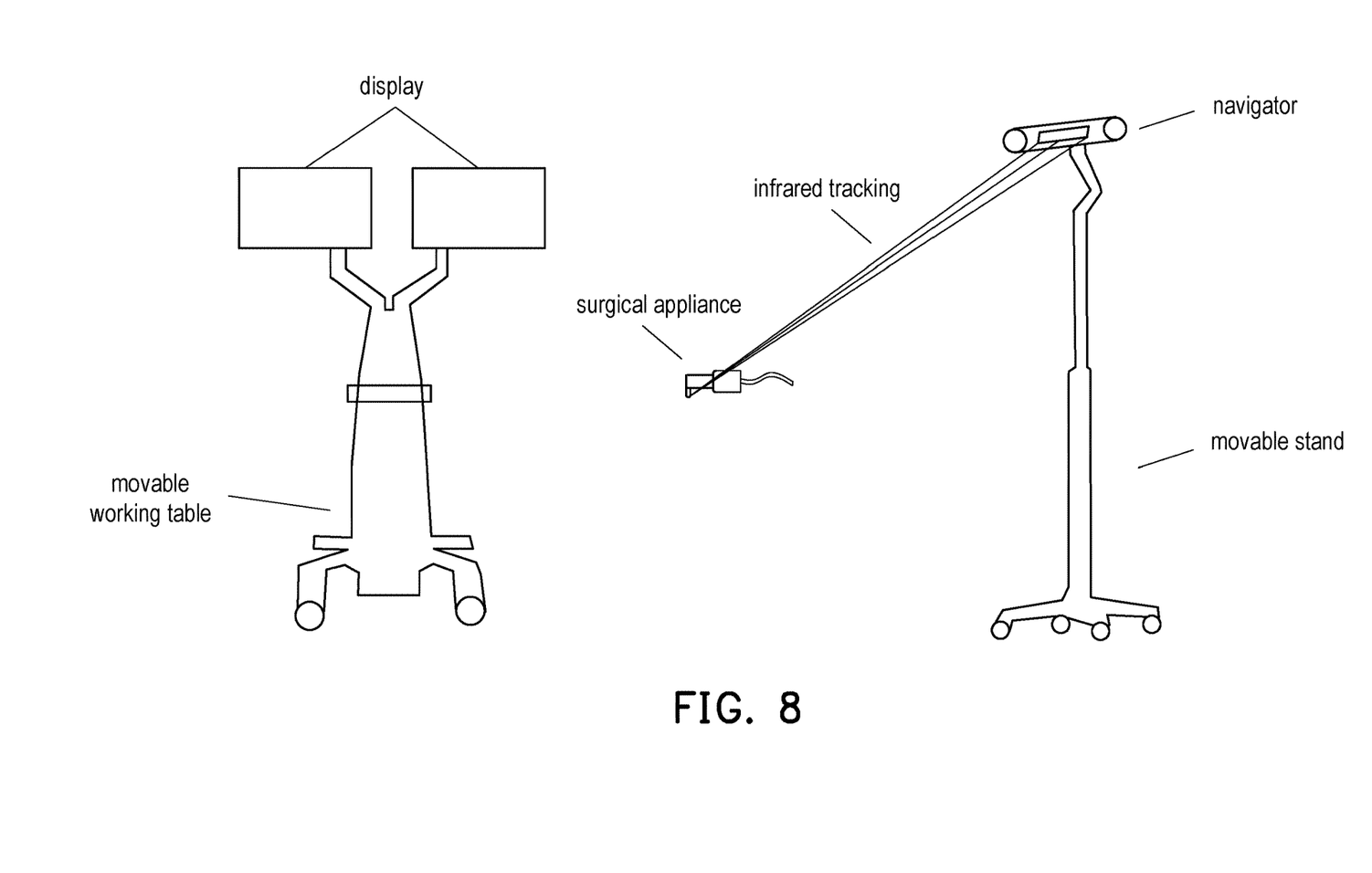
FIG. 8 a schematic diagram illustrating real-time guide of surgical operation by a navigator in a pulp diagnosis-treatment assistance system based on digital dynamic guide according to an embodiment of the present disclosure.

As shown in FIGS. 6 to 8, the navigator, the surgical appliance and a surgical zone tracking positioning apparatus can be used to detect and obtain the position information of the surgical appliance and the relative position information of the surgical zone.

In the embodiments of the present disclosure, based on CBCT, the oral scanner and the oral microscope, three-dimensional reconstruction of the oral model is performed such that the medical staff can accurately know where the surgical appliance is based on the positioning technology of the surgical appliance. In this way, the medical staff is assisted in performing pulp diagnosis and treatment.

Preferably, the image displaying apparatus is a naked eye 3D display.

Preferably, the image displaying apparatus is a microscopic ocular.

The microscopic ocular is configured to be in the form of head-mounted AR display device.

Specifically, the CBCT three-dimensional reconstruction data is obtained by performing detection on the oral cavity of the patient using the CBCT device before pulp diagnosis and treatment.

The three-dimensional model data of the oral scanner is obtained by performing detection on the oral cavity of the patient using the oral scanner before pulp diagnosis and treatment.

Based on the technical solution provide by the embodiments of the present disclosure, there is provided an implementation which is described below.

First of all, a CBCT image of the oral cavity of the patient, i.e. the CBCT three-dimensional reconstruction data and the data of the oral scanner, i.e. the three-dimensional model data of the oral scanner are received, and analyzed by using a preset signal processing apparatus. Then comparison of biological characteristics is performed based on image processing algorithm to perform integration and registration based on feature points, so as to obtain an accurate three-dimensional perspective model image of the oral cavity of the target object. Thus, the integrated and registered three-dimensional model data is obtained.

The oral CBCT image has the of stereoscopic perspective, and low-resolution characteristics, whereas the data of the oral scanner has the of stereoscopic non-perspective and high-resolution characteristics.

Secondly, a three-dimensional digital image is obtained by collecting an optical image under the oral microscope, namely, the digital scanning image of the oral microscope is obtained and then observed by the head-mounted AR display device or the naked eye 3D display, or directly displayed in the field of view of the operator in the form of optical image by the microscopic ocular.

When wearing the AR display device or the naked eye 3D display, the doctor can move his head freely without any limitation by the position of the surgical microscope, and can simultaneously observe the under-microscope magnified field of view and outside-microscope normal field of view, the surgical appliance being continuously visible and accurately being moved to a specified position under the microscope.

The under-microscope magnified field of view is the display region of a display module in the AR, the naked eye 3D display and the ocular, and the outside-microscope normal field of view is a display region of a real image displayed by a non-display module.

At the same time, a patient state can be observed or guidance is provided to a nurse to confirm the appliance or material is correct.

An image split screen display module displays the above information on the head-mounted AR display device or the naked eye 3D display or the ocular display device in superimposition form. Each display window can be opened or closed, and their sizes and positions can be adjustable, and if necessary, four views can be generated, which are three plane views of sections of three directions and one stereoscopic perspective view to display relative position information of the surgical appliance and the target object. The doctor can mark a virtual positioning point on the model, for example, the position of the root canal orifice, the endodontic access, the window opening position, the removal scope, and so forth, so as to guide various operations.

The guiding way may be performed in the following two methods.

In a first method, color partitioning is performed on different tissues of the surgical zone, such that the operator can observe, in real time, the operation position of the appliance under the microscope through the head-mounted AR and the naked eye 3D display.

In a second method, marking designing is performed in advance for the operation path before surgery, and then three-dimensional perspective model registration is performed. The pre-surgical planned path can be displayed through display devices such as head-mounted AR, naked eye 3D display, and so forth to guide the operator in surgical operation.

Marking designing is performed in advance for the operation path before surgery, and registration and calibration are performed for the oral tissues and the surgical appliance; corresponding positions of the surgical zones of the surgical appliance are tracked by using the navigator; the pre-surgical planned path can be displayed through display devices such as head-mounted AR, naked eye 3D display, and so forth to guide the operator in surgical operation.

In the embodiments of the present disclosure, the optical image under the dental microscope is displayed in the field of view of the operator in the form of optical image, and the operation space of the doctor will no longer be affected by the position of the microscope. In the meantime, the state of the patient can be observed and guidance is provided for other surgical personnel.

The integrated and registered three-dimensional model data can be superimposed with the digital scanning image of the oral microscope for displaying, and a positioning and navigation detection apparatus is disposed in the surgical appliance to obtain the digital scanning image of the oral microscope so as to visually observe information of different tissues in the surgical zone; or, marking designing is performed in advance for the operation path before surgery, and registration and calibration are performed for the oral tissues and the surgical appliance, and corresponding positions of the surgical zones of the surgical appliance are tracked by using the navigator, so as to guide accurate surgical operation. In this way, minimally-invasive, accurately-controllable, and visually-efficient dental pulp operation based on three-dimensional digital guide can be achieved under the oral microscope.

It shall be noted that the relational terms such as "first" and "second" used herein are merely intended to distinguish one entity or operation from another entity or operation rather than to require or imply any such actual relation or order existing between these entities or operations. Also, the term "including", "containing" or any variation thereof is intended to encompass non-exclusive inclusion, so that a process, method, article, or device including a series of elements includes not only those elements but also other elements not listed explicitly or those elements inherent to such a process, method, article, or device. Without more limitations, an element defined by the statement "including a . . . " shall not be precluded to include additional same elements present in a process, method, article, or device including the elements.

The above descriptions are made only to specific embodiments of the present disclosure which can enable one of ordinary skill in the art to understand or implement the present disclosure. It is obvious for one of ordinary skill in the art that various modifications can be made to these embodiments. A general principle defined herein can be implemented in other embodiments without departing from the spirit or scope of the present disclosure. The present disclosure will not be limited to these embodiments shown in the present disclosure but shall conform to the widest scope consistent with the principle and the novel features of the present disclosure.

What is claimed is:

1. A pulp diagnosis-treatment assistance method based on digital dynamic guide, comprising the following steps:
    based on CBCT (Cone Beam Computerized Tomography) three-dimensional reconstruction data and three-dimensional model data of an oral scanner corresponding to an oral cavity of a patient, obtaining integrated and registered three-dimensional model data;
    obtaining a digital scanning image of an oral microscope corresponding to the oral cavity of the patient;
    based on the CBCT three-dimensional reconstruction data corresponding to the oral cavity of the patient and a pre-surgical designed surgical path, obtaining position information of a surgical appliance and relative position information of the surgical zone;
    based on the integrated and registered three-dimensional model data, the digital scanning image of the oral microscope, the position information of the surgical appliance and the relative position information of the surgical zone, obtaining a diagnosis-treatment assistance image, displaying the diagnosis-treatment assistance image by an image displaying apparatus, and based on the diagnosis-treatment assistance image, performing a pulp diagnosis and treatment assistance.

2. The method according to claim 1, wherein based on the integrated and registered three-dimensional model data, the digital scanning image of the oral microscope, the position information of the surgical appliance and the relative position information of the surgical zone, obtaining the diagnosis-treatment assistance image, and based on the diagnosis-treatment assistance image, performing the pulp diagnosis and treatment assistance comprise the following steps:
    based on the integrated and registered three-dimensional model data, the digital scanning image of the oral microscope, the position information of the surgical appliance and the relative position information of the surgical zone, obtaining a corresponding diagnosis-treatment assistance image;
    displaying the corresponding diagnosis-treatment assistance image by a display device.

3. The method according to claim 2, wherein, the display device is a naked eye 3D display.

4. The method according to claim 1, wherein based on the integrated and registered three-dimensional model data, the digital scanning image of the oral microscope, the position information of the surgical appliance and the relative position information of the surgical zone, obtaining the diagnosis-treatment assistance image, and based on the diagnosis-treatment assistance image, performing the pulp diagnosis and treatment assistance comprise the following steps:
    based on the integrated and registered three-dimensional model data, the position information of the surgical appliance and the relative position information of the surgical zone, performing image superimposition to obtain a corresponding integrated and registered three-dimensional optical image; and,
    based on the corresponding integrated and registered three-dimensional optical image and the digital scanning image of the oral microscope, obtaining a corresponding diagnosis-treatment assistance image;
    observing the corresponding diagnosis-treatment assistance image by using a microscopic ocular.

5. The method according to claim 4, wherein, the microscopic ocular is configured to be in the form of a head-mounted AR display device.

6. The method according to claim 1, wherein, the CBCT three-dimensional reconstruction data is obtained by performing detection on the oral cavity of the patient using a CBCT device before the pulp diagnosis and treatment;
    the three-dimensional model data of the oral scanner is obtained by performing detection on the oral cavity of the patient using the oral scanner before the pulp diagnosis and treatment.

7. A pulp diagnosis-treatment assistance system based on digital dynamic guide, comprising:
    a CBCT device, configured to detect and obtain CBCT three-dimensional reconstruction data corresponding to an oral cavity of a patient;
    an oral scanner, configured to detect and obtain three-dimensional model data of the oral scanner corresponding to the oral cavity of the patient;
    an oral microscope, configured to detect and obtain a digital scanning image of the oral microscope corresponding to the oral cavity of the patient;
    an image integrating apparatus, configured to, based on the CBCT three-dimensional reconstruction data corresponding to the oral cavity of the patient and the three-dimensional model data of the oral scanner corresponding to the oral cavity of the patient, obtain integrated and registered three-dimensional model data;
    a navigator, configured to, based on the CBCT three-dimensional reconstruction data corresponding to the oral cavity of the patient and a pred-surgical designed surgical path, obtain position information of a surgical appliance and relative position information of a surgical zone;

wherein the image integrating apparatus is further configured to, based on the integrated and registered three-dimensional model data, the digital scanning image of the oral microscope, the position information of the surgical appliance and the relative position information of the surgical zone, a diagnosis-treatment assistance image is obtained;

an image displaying apparatus, configured to display the diagnosis-treatment assistance image for performing a pulp diagnosis and treatment assistance.

8. The system according to claim 7, wherein, the image displaying apparatus is a naked eye 3D display.

9. The system according to claim 7, wherein, the image displaying apparatus is a microscopic ocular; the microscopic ocular is configured to be in the form of a head-mounted AR display device.

10. The system according to claim 7, wherein, the CBCT three-dimensional reconstruction data is obtained by performing detection on the oral cavity of the patient using a CBCT device before a pulp diagnosis and treatment; the three-dimensional model data of the oral scanner is obtained by performing detection on the oral cavity of the patient using the oral scanner before the pulp diagnosis and treatment.

\* \* \* \* \*